United States Patent [19]
Yabe et al.

[11] Patent Number: 4,862,872
[45] Date of Patent: Sep. 5, 1989

[54] ENDOSCOPE AND ENDOSCOPE WASHING APPARATUS

[75] Inventors: Hisao Yabe; Masahide Kanno, both of Hachioji; Jun Yoshinaga, Hino; Takeshi Yokoi; Kazuhiko Ozeki, both of Hachioji; Takeaki Nakamura, Hino; Yoshikazu Tojo, Hachioji; Shinichi Nishigaki, Tokyo; Hiromasa Suzuki, Akishima, all of Japan

[73] Assignee: Olympus Optical Co., Ltd., Tokyo, Japan

[21] Appl. No.: 178,683

[22] Filed: Apr. 6, 1988

[30] Foreign Application Priority Data

Apr. 17, 1987 [JP] Japan .................................. 62-094446
Jun. 11, 1987 [JP] Japan .................................. 62-145531

[51] Int. Cl.$^4$ .............................................. A61B 1/12
[52] U.S. Cl. ....................................................... 128/6
[58] Field of Search ........................................ 128/4, 6

[56] References Cited

U.S. PATENT DOCUMENTS 4,402,310 9/1983 Kimura .................................. 128/4
4,509,507 4/1985 Yabe ...................................... 128/4

Primary Examiner—William H. Grieb
Attorney, Agent, or Firm—Armstrong, Nikaido, Marmelstein, Kubovcik & Murray

[57] ABSTRACT

This endoscope system comprises an endoscope and a washing apparatus. The endoscope is provided with an elongate insertable part having an observing window and illuminating window in the tip part, an observing system receiving the returning light from an object entering through the observing window, an illuminating light output system emitting an illuminating light from the illuminating window and a memorizing device capable of memorizing information relating to washing. The washing apparatus is provided with a read-out device reading out information memorized in the memorizing device of the endoscope and a control device controlling the conditions of washing the endoscope by the information read out by the read-out device.

26 Claims, 14 Drawing Sheets

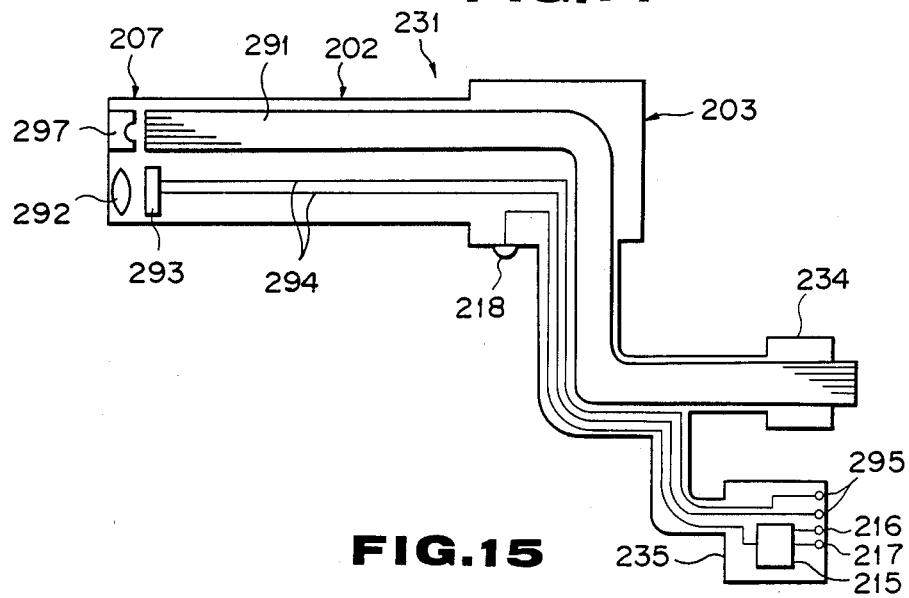
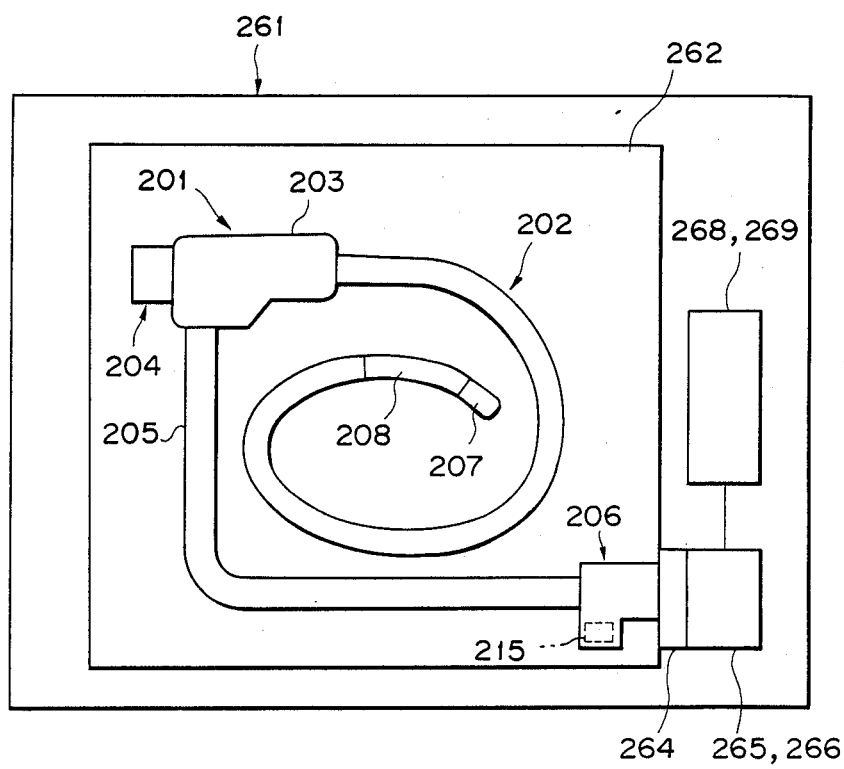

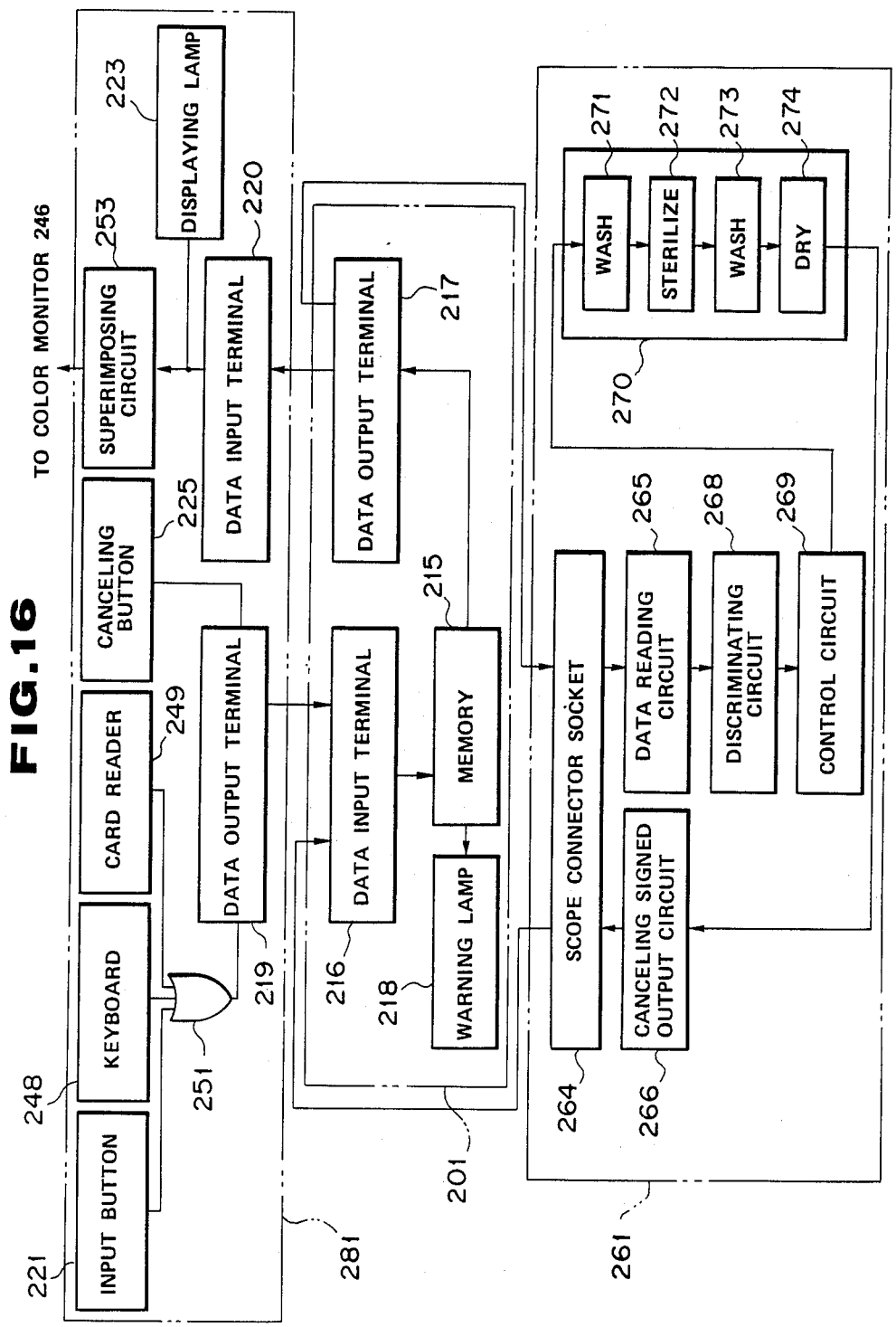

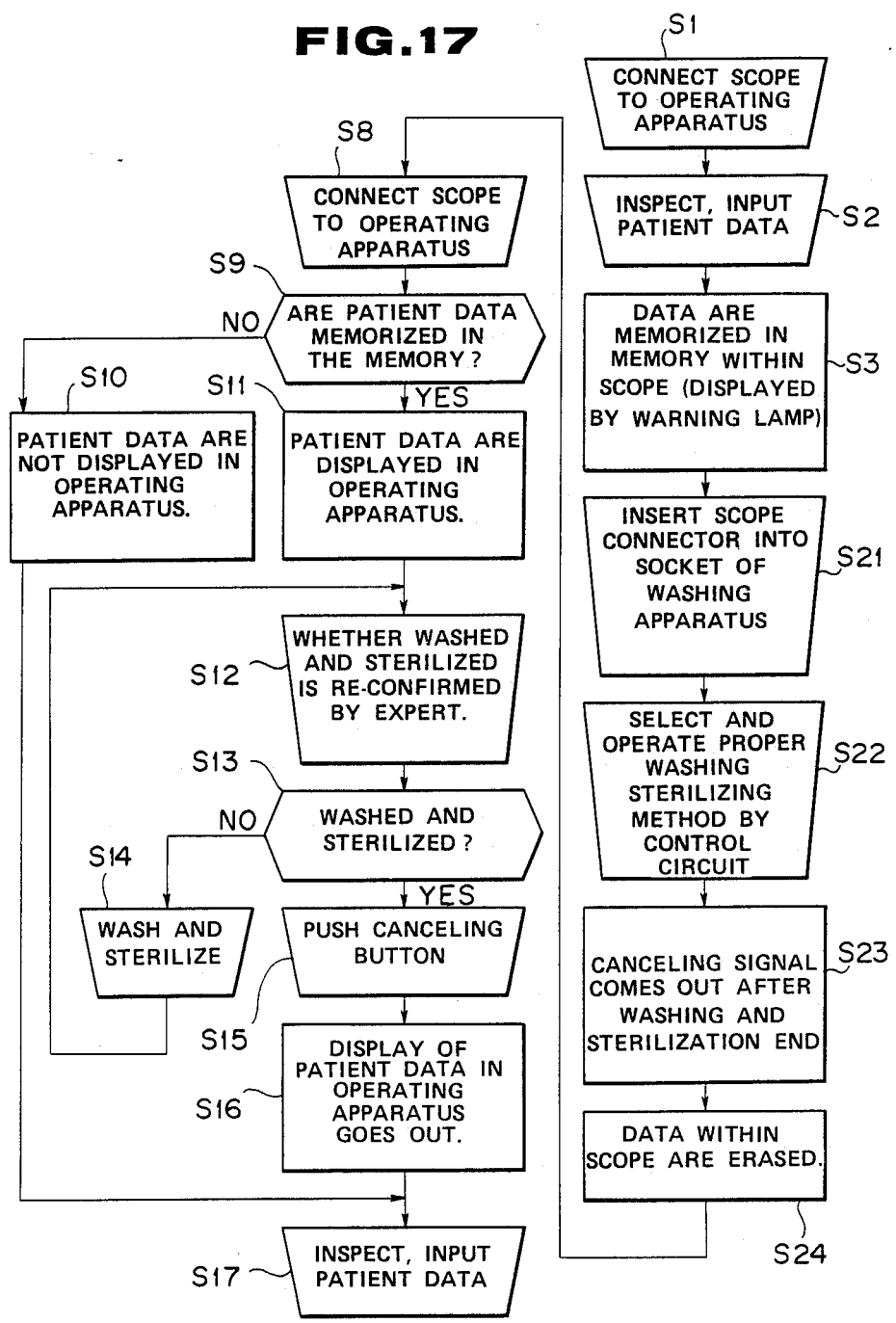

ENDOSCOPE AND ENDOSCOPE WASHING APPARATUS

BACKGROUND OF THE INVENTION

1. Field of the Invention

This invention relates to an endoscope and a washing apparatus adapted to wash the endoscope.

2. Related Art Statement

Recently, there is extensively used an endoscope whereby organs within a body cavity can be observed by inserting an elongate insertable part through the body cavity and various curing treatments can be made by using treating tools inserted through a treating tool channel as required.

It is indispensable to wash and sterilize the above mentioned endoscope particularly in case it is inserted into a living body.

Generally different kinds of endoscopes are often used in response to the using positions. Whether the endoscope is heatproof or not, the degree of the heat-proofness, the proofness against the sterilizing liquid and the water-proofness are different depending on the kinds of endoscopes.

In the washing function, when the washing water temperature is made higher, not only a higher washing function but also a sterilizing function by heat will be able to be expected. In the case of the warm wind drying, not only the trouble of wiping off water drops deposited on the endoscope will not be required but also the growth of germs deposited on the endoscope will be able to be inhibited.

From the above mentioned reasons, it is desirable to warn water-wash or warm wind-dry (hot wind-dry) the endoscope. However, on the other hand, in case an endoscope having no heat-proofness is washed in warm water or dried with warm wind, the endoscope will be likely to be broken.

It is also desirable to sterilize the endoscope by using a stronger sterilizing liquid for a longer time but an endoscope having no proofness is likely to be broken.

After the above mentioned endoscope is used on a patient of a disease likely to be infected by B-type liver fever, amoeba dysentery or AIDS, it is always necessary to disinfect and sterilize the endoscope to prevent the secondary infection.

However, there have been problems that the information as to on what patient the endoscope has been used can not be recorded in the above mentioned endoscope and whether the endoscope has been used on a patient likely to be infected unless the endoscope is sterilized immediately after it is used or how the endoscope should be sterilized is not known.

OBJECT AND SUMMARY OF THE INVENTION

An object of the present invention is to provide an endoscope whereby the information on the proofness of the endoscope and the washing after the use on the patient can be confirmed so that the endoscope may be properly washed and sterilized.

Another object of the present invention is to provide an endoscope system consisting of an endoscope and an endoscope washing apparatus and adapted to properly wash the endoscope in response to the information on washing.

The endoscope system of the present invention is provided with an endoscope and a washing apparatus. The above mentioned endoscope comprises an elongate insertable part having an observing window and illuminating window in the tip part, an observing means for observing an object by receiving a returning light from the object entering through the observing window, an illuminating light output means emitting an illuminating light from the illuminating window and a memorizing means capable of memorizing the information on washing. The above mentioned washing apparatus is provided with a read-out means for reading out the information memorized by the memorizing means of the above mentioned endoscope and a control means controlling the conditions of washing the above mentioned endoscope by the information read out by this read-out means.

By the way, in the present invention, the term "washing" shall include washing with water or washing water, disinfection, sterilization, rinsing and drying. The other features and advantages of the present invention will become apparent enough with the following explanation.

BRIEF DESCRIPTION OF THE DRAWINGS

FIG. 1 is an explanatory view showing the formation of an endoscope system.

FIG. 2 is an explanatory view showing the formation of a washing apparatus.

FIG. 3 is an explanatory view showing the formation of a fiber scope.

FIG. 8 is an explanatory view showing the formation of an endoscope system. FIG. 9 is a view as seen in the direction indicated by the arrow Y in FIG. 8.

FIG. 10 is a block diagram showing an essential part of an endoscope system.

FIG. 11 is a flow chart showing the operation and action of an endoscope system.

FIGS. 12 to 14 relate to the seventh embodiment of the present invention.

FIG. 12 is an explanatory view showing the formation of an endoscope system.

FIG. 13 is a block diagram showing the essential part of an endoscope system.

FIG. 14 is an explanatory view showing the formation of an electronic scope.

FIGS. 15 to 17 relate to the eighth embodiment of the present invention.

FIG. 15 is an explanatory view showing a washing apparatus.

FIG. 16 is a block diagram showing the essential part of an endoscope system.

FIG. 17 is a flow chart showing the operation and action of an endoscope system.

Figure 1:
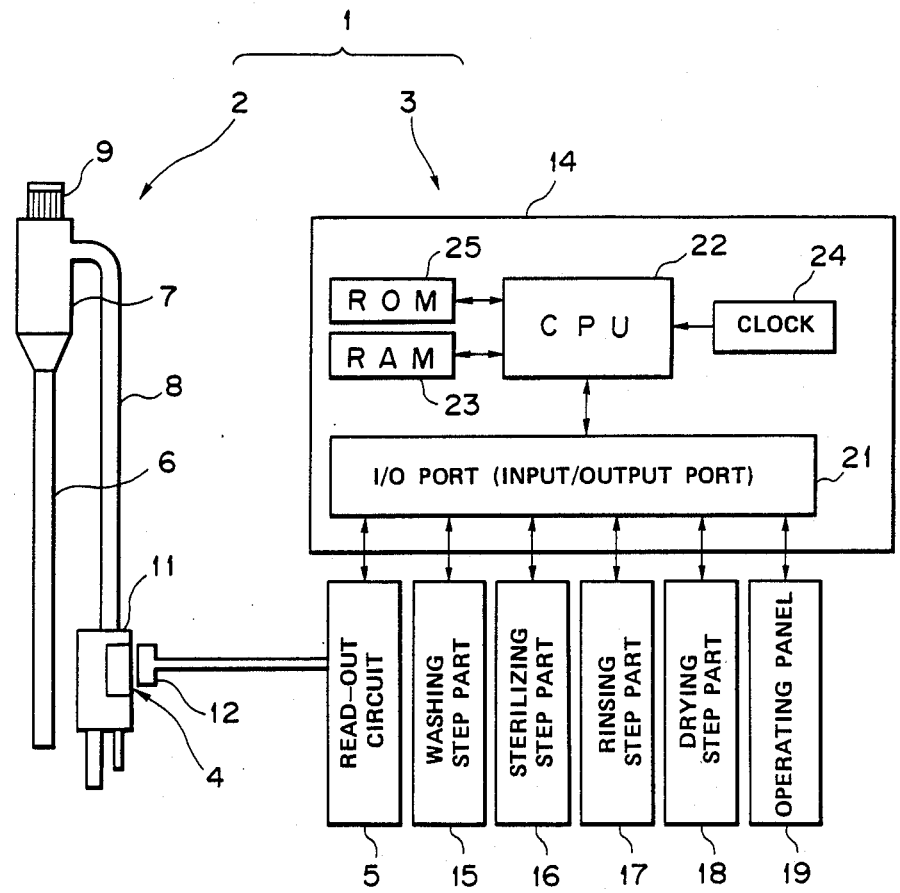
FIGS. 1 to 3 relate to the first embodiment of the present invention.
Figure 2:
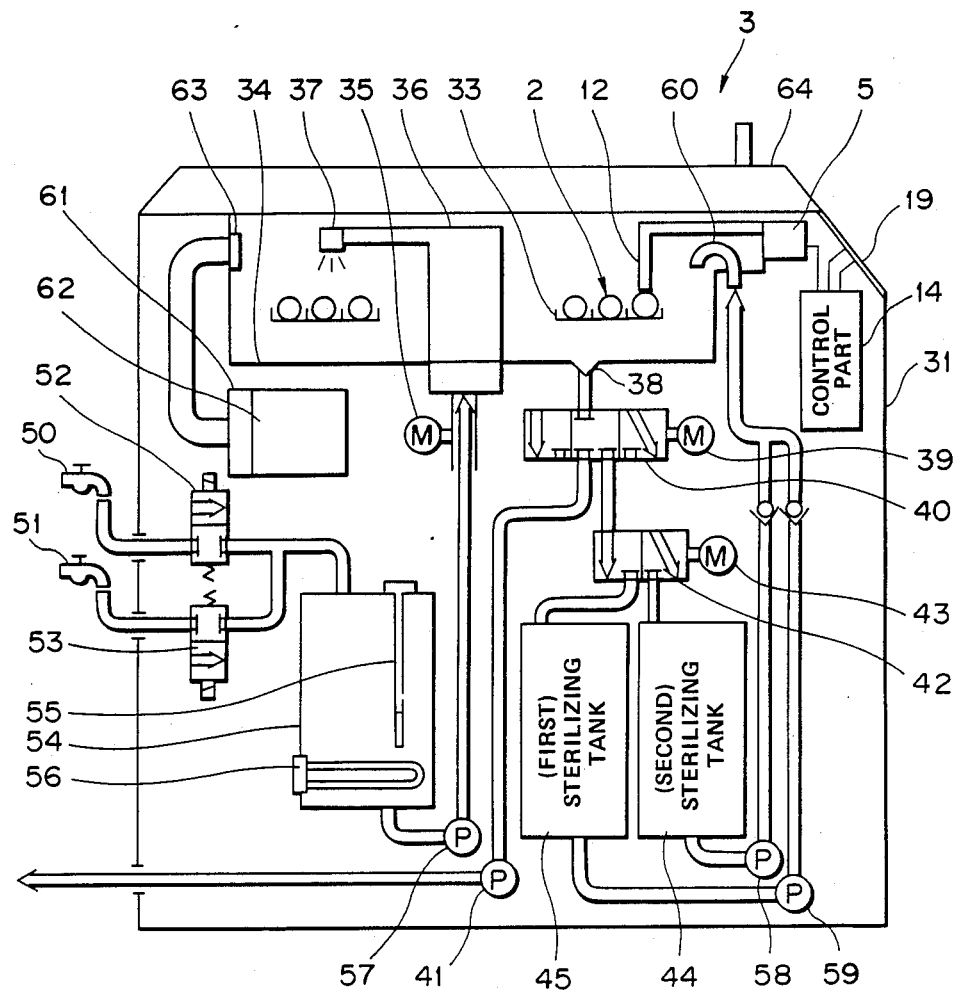
Figure 3:
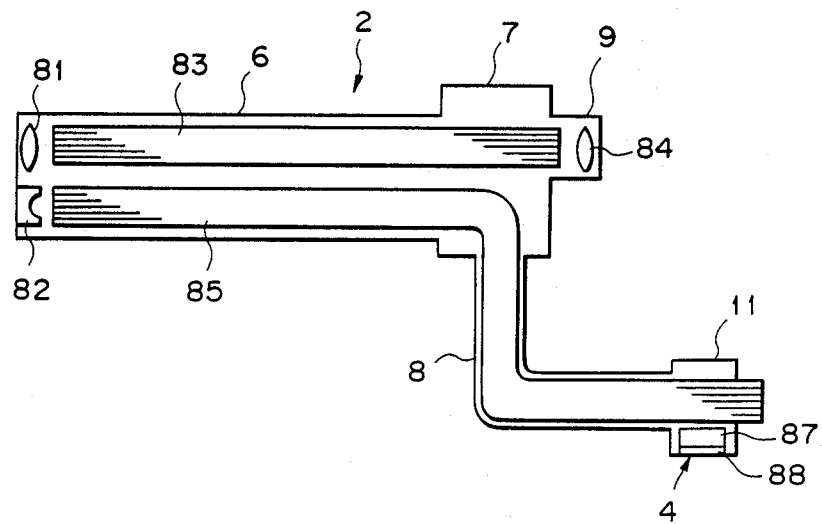

DETAILED DESCRIPTION OF THE PREFERRED EMBODIMENTS:

FIGS. 1 to 3 show the first embodiment of the present invention.

As shown in FIG. 1, an endoscope system 1 of the first embodiment comprises an endoscope 2 and an endoscope washing apparatus 3 for washing and sterilizing this endoscope 2, characterized in that the above mentioned endoscope 2 is provided with a proofness data memorizing part 4 and the (endoscope) washing apparatus 3 is provided with a circuit 5 for reading out the data memorized in this memorizing part 4 so that such step as washing the endoscope 2 may be controlled to be proper for the endoscope 2.

The above mentioned endoscope 2 comprises an elongate insertable part 6 insertable into a body cavity, a thick operating part 7 formed on the rear end side of this insertable part 6, a light guide cable (or universal cord) 8 extended out of this operating part 8 and an eyepiece part 9 formed at the rear end of the above mentioned operating part 7 and a light guide connector 11 is formed in the end part of the above mentioned light guide cable 8.

The interior of the above mentoned endoscope 2 is formed as shown in FIG. 3.

An objective lens 81 and illuminating lens 82 are arranged in the tip part of the insertable part 6. The tip surface of an image guide 83 consisting of a fiber bundle is arranged in the image forming position of the above mentioned objective lens 81. This image guide 83 is inserted through the above mentioned insertable part 6, is extended to the above mentioned eyepiece part 9 and is opposed on the rear end surface to an eyepiece 84 provided within the above mentioned eyepiece part 9. A light guide 85 consisting of a fiber bundle is provided as connected on the rear end side of the above mentioned illuminating lens 82, is inserted through the above mentioned insertable part 6, operating part 7 and light guide cable 8 and is connected to a light guide connector 11. When the above mentioned light guide connector 11 is connected to a light source apparatus not illustrated, the illuminating light form this light source apparatus will enter the entrance end of the above mentioned light guide 85, will be led to the tip part of the insertable part 6 by the above mentioned light guide 85, will be emitted from the exit end surface and will be radiated onto an object through the illuminating lens 82. The returning light from the object by this illuminating light will be made to form an image on the tip surface of the image guide 83 by the objective lens 81. This object image will be led to the eyepiece part 9 by the above mentioned image guide 83 and will be observed through the eyepiece 84.

The above mentioned connector 11 is provided with a memorizing part 4 which consists, for example, of a latch 87 memorizing data and a contact 88 connected to the data output end. This contact 88 is made to read out the data written into the latch 87 by connecting a contact 12 provided at the end of a cord extended out of the read-out circuit 5.

The functional formation of the washing apparatus 3 provided with the above mentioned read-out circuit 5 is shown in FIG. 1.

That is to say, the washing apparatus 3 comprises a control part 14 controlling the washing process on the basis of the data read out of the read-out circuit 5, a washing step part 15 controlled by this control part 14, a sterilizing step part 16, a rinsing step part 17, a drying step part 18 and an operating panel 19.

The above mentioned read-out circuit 5 reads out the data of the memorizing part 4, that is, such data as whether the endoscope is heat-proof or not, the heat-proof temperature, chemicals-proofness (usable chemicals and dipping time) and water-proofness and transfers these read out data to a central process unit (abbreviated as CPU hereinafter) 22 through an I/O port (input/output port) within the control part 14. The data transferred to this CPU 22 are stored, for example, in a random access memory (abbreviated as RAM hereinafter) 23. The data part required in the case of the washing process is read out of the RAM 23 by the program of the program data written into a ROM 25 as synchronized with the clock of a clock generator 24 so that the endoscope 2 from which the data have been read out, that is, the endoscope 2 to be actually washed may be properly washed.

The concrete formation of the above mentioned washing apparatus 3 is shown in FIG. 2.

A washing sterilizing tank 34 containing holding members 33 holding the endoscopes 2 is provided within the body 31 of the washing apparatus 3 and a rotary head 36 rotating with a motor 35 as a driving source is provided substantially in the center of this washing sterilizing tank 34. A nozzle 37 jetting washing water and rinsing water toward the endoscope 2 is provided on this rotary head 36. A drain port 38 is provided in the bottom of the washing sterilizing tank 34. A three-way switching valve 40 driven by a motor 39 is provided below this drain port 38.

This three-way switching valve 40 can select three kinds of states of a state of leading drain water drained from the washing sterilizing tank 34 to a drain pump 41, a state of leading a drained sterilizing liquid to a switching valve 42 and a state of intercepting the water path.

The switching valve 42 is driven by a motor 43 to inject the sterilizing liquid flowing in through the three-way switching valve 40 selectively into a first sterilizing tank 44 and second sterilizing tank 45. A contact 12 of the read-out circuit 5 reading out the information of the memorizing part 4 within the endoscope 2 is provided within the washing sterilizing tank 34. The contact 12 is connected to the control part 14 through the read-out circuit 5. The control part 14 is electrically connected with the operating panel 19 and, though not particularly illustrated, each pump, motor, valve, fan, heat source for warm water or warm wind and temperature detecting sensor.

Now, feed water and warm water fed respectively through a feed water tap 50 and warm water feeding tap 51 are stored in a feed water tank 54 through a feed water valve 52 and warm water feeding valve 53 opening and closing respective flow paths.

Here, a sensor 55 sensing the liquid temperature within the feed water tank 54 and a heater 56 for warming are provided within the feed water tank 54.

The washing water stored in the above mentioned feed water tank 54 is pressed by a washing pump 57, is jetted into the washing sterilizing tank 34 through the nozzle 37 of the rotary head 36 and washes the endoscope 2 part in the position opposed to the nozzle 37. After being jetted onto these endoscopes 2, the washing water accumulated in the washing sterilizing tank 34 is transmitted to a drain pump 41 through the three-way switching valve 40, is pressed and is drained out.

The sterilizing liquids within the first sterilizing tank 44 and second sterilizing tank 45 are pressed respectively by sterilizing liquid pumps 58 and 59 and are injected into the washing sterilizing tank 34 through an injecting port 60.

By the way, after the washing or sterilization by injecting the sterilizing liquid, a washing step, that is, a rinsing step is made without injecting the sterilizing liquid.

As a means of drying the endoscope 2 after the rinsing by jetting rinsing water or warm water from the above mentioned nozzle 37, air warmed by a heater 61 is pressed by a flower 62 and is fed to the washing sterilizing tank 34 through an air feeding port 63 through an air feeding pipe to dry the wet endoscope 2.

By the way, an opening and closing cover 64 is provided above the washing sterilizing tank 34 so that the endoscope 2 may be held by the holding member 33 or taken out through it after the washing.

The operation of the thus formed first embodiment shall be explained in the following.

The cover 64 of the washing apparatus 3 is opened and the used endoscope 2 is contained and held in the spiral containing part of the holding member 33. In this case, the memorizing part 4 of the light guide connector 11 is set in contact with the read-out contact 12 of the read-out circuit 5. When the cover 64 is closed and the switch of the washing operation of the operating panel 19 is switched on, the read-out circuit 5 will read out such proofness data memorized in advance in the memorizing part 4 of the contained endoscope 2 as whether the endoscope is heat-proof or not, the heat-proof temperature, chemicals-proofness and water-proofness, the read out data will be input into the CPU 22 through the I/O port 21 within the control part 14 as shown in FIG. 1 and this CPU 22 will store the data in the RAM 23.

In the case of the washing operation, the CPU 22 will refer to the data parts (read out of the RAM 23) required to carry out the respective steps in the above mentioned data and will carry out the washing process corresponding to the proofness of the endoscope 2.

For example, if the contained and held endoscope 2 is not heat-proof, it will be distinguished not to be heat-proof and the following washing step will be made.

The feed water valve 52 will be opened, tap water from the feed water tap 50 will be fed into the feed water tank 54 and the endoscope will be washed with tap water.

On the other hand, in case the endoscope is heat-proof, the warm water feeding valve 53 will be opened, warm water from the warm water feeding tap 41 will be fed to the feed water tank 54 and the endoscope will be washed with warm water.

In case the warm water feeding temperature is lower than a predetermined temperature, the warm water within the feed water tank 54 will be heated by the heater 56 to a predetermined temperatures against which the endoscope 2 is proof and the endoscope will be washed with warm water at this temperature.

When the washing step thus ends, the next sterilizing step will begin. Before beginning this step, the CPU 22 will read out the data of chemicals-proofness stored within the RAM 23 and will make a sterilizing step with the chemicals adapted to the chemicals-proofness of the endoscope 2.

For example, if the endoscope 2 is proof against the chemicals stored in the first sterilizing tank 44 or second sterilizing tank 45, the sterilizing pump 58 or 59 communicating with the sterilizing tank 44 or 45 containing the chemicals against which the endoscope 2 is proof will be set in the operating mode, the chemicals will be pressed and injected into the washing sterilizing tank 34 through the injecting port 60 to sterilize the endoscope.

When the sterilizing step thus ends, a rinsing step will begin. In this rinsing step, the endoscope is washed with tap water or warm water on the basis of the heat-proofness data contained in the RAM 23 without using chemicals and is rinsed sufficiently to leave no chemicals as deposited on the endoscope.

When the rinsing step thus ends, the next drying step will begin.

Before beginning this drying step, the CPU 22 will refer to the data of the RAM 23 and will discriminate whether the endoscope is heat-proof or not. In case it is heat-proof, it will be dried with warm wind. In case it is not heat-proof, it will be dried with cool wind (with blowing not heated).

In case it is dried with the above mentioned warm wind (hot wind), the heater 61 will be set in operation and warmed wind will be fed into the washing sterilizing tank 34 with the blower 62. In the case of drying by blowing, the endoscope will be dried by blowing without operating the heater 61.

According to the thus operating first embodiment, the proofness data required to wash or sterilize the endoscope 2 contained in the washing apparatus 3 are read out and the washing step and sterilizing step are controlled on the basis of the read out data. Therefore, even in case the endoscope is different in the proofness, the washing and sterilization most adapted to the endoscope will be able to be made and the endoscope will be able to be prevented from being broken or being reduced in the life.

Further, in the case of the washing operation, any difficult adjustment or selecting operation will not be required.

Figure 4:
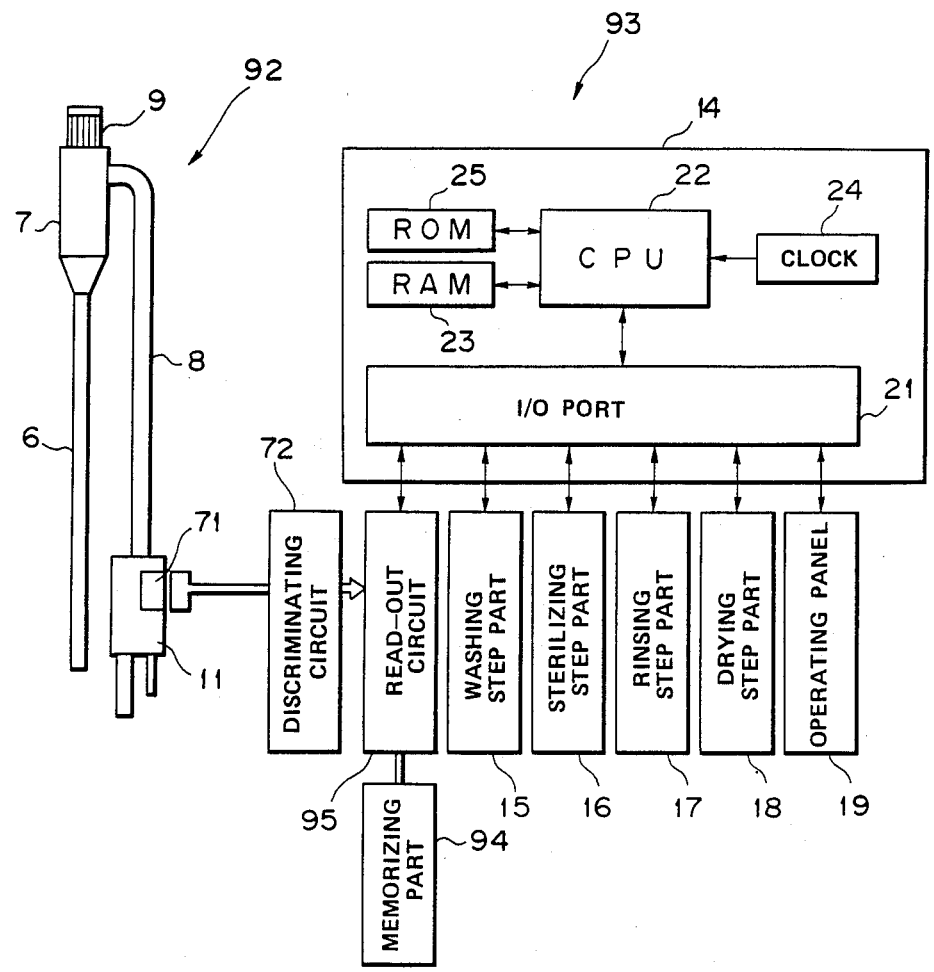
FIG. 4 is an explanatory view showing the formation of an endoscope system in the second embodiment of the present invention.

FIG. 4 shows the second embodiment of the present invention.

In this second embodiment, the light guide connector 11 of an endoscope 92 is provided with an endoscope discriminating code part 71 as a memorizing means. On the other hand, a washing apparatus 93 is provided with a discriminating circuit 72 discriminating the codes of the above mentioned code part 71. The endoscope discriminating signal discriminated by this discriminating circuit 72 is input into a read-out circuit 95. This read-out circuit 95 reads out the proofness data memorized as in response to the discriminating signal in advance from a memorizing part 94 on the basis of the discriminating signal and inputs them into the CPU 22 through the I/O port 21.

The other formations are the same as in the first embodiment.

The operations and effects of this second embodiment are substantially the same as of the above mentioned first embodiment. However, as only the discriminating code part 71 may be provided on the endoscope 92 side, the part of this discriminating code part 71 can be formed to be a small part and even the case that the information relating to the proofness of the endoscope is regulated in detail and the information amount is large can be simply coped with.

By the way, a ROM IC can be used for the above mentioned memorizing part 94.

Also, a bar code may be used on the outer surface for the memorizing part 94 or discriminating cord part 71 so that the data may be read out by a bar code reader. Also, any other means utilizing a laser holograph or magnetism or provided with concavo-convexes may be used and a reading means in response to it may be formed.

By the way, in the above mentioned respective embodiments, the memorizing part 94 or code part 71 provided in the endoscope 92 may be provided not only in the light guide connector 11 part but also in the universal cord connector part, operating part or insertable part of the electronic scope.

By the way, the memorizing part 94 may be filled with information so that the temperature of washing water and rinsing water may be minutely set in response to the heat-proofness of the endoscope. Further, it may be filled with information on the pressure-proofness of washing water and rinsing water. Further, the information on the kind, concentration, dipping time and operating temperature of the sterilizing liquid used in the sterilizng method can be also written in. Also, the information on the water-proofness as to whether total washing is possible or not or the drying temperature may be memorized so that such information may be referred to in reading out and the most adapted washing or sterilization may be made.

As described above, according to the first and second embodiments, the endoscope side is provided with proofness data of the endoscope or discriminating codes corresponding to the proofness data and, on the other hand, the washing apparatus side is provided with a read-out means capable of reading out the above mentioned proofness data so that the endscope may be washed or sterilized on the basis of the proofness data. Even an endoscope different in the proofness can be washed or sterilized as adapted to it.

Figure 5:
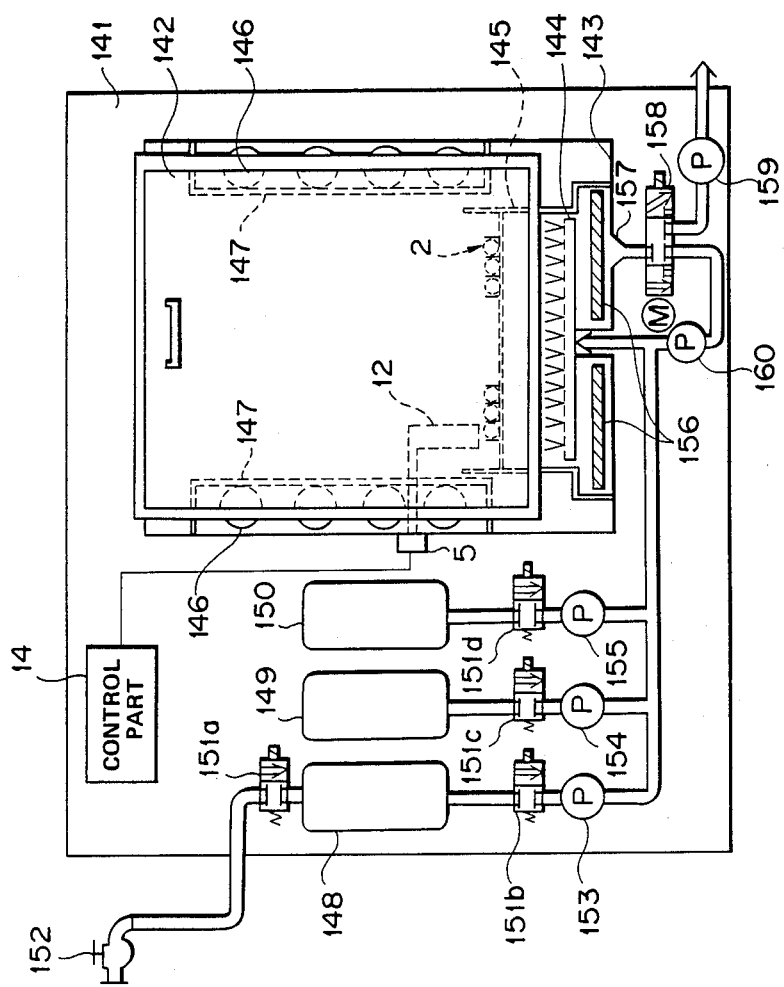
FIG. 5 is an explanatory view showing the formation of a washing apparatus in the third embodiment of the present invention.

FIG. 5 shows the third embodiment of the present invention.

The reference numeral 141 represents a washing apparatus body. A washing door 142 is provided on the side surface part of this washing apparatus body 141 so as to be able to be opened and closed. A washing tank 143 is provided inside the washing door 142. A jetting nozzle 144 in which many nozzle orifices are arranged in a row is rotatably provided in the center of this washing tank 143 and a mounting stand 145 on which the endoscope 2 to be washed is to be mounted is provided further above the jetting nozzle 144. A sterilizing lamp 146 generating ultraviolet rays and contained in a protective case 147 is provided on the inside wall part of the washing tank 143. By the way, the protective case 147 is formed of such material high in the ultraviolet ray permeability as, for example, an ultraviolet band pass filter or quartz glass.

Also, a feed water tank 148, detergent tank 149 and sterilizing liquid tank 150 are provided within the apparatus body 141. A tap 152 is connected to the above mentioned feed water tank 148 through an electromagnetic valve 151a. The washing water fed from this tap 152 is stored in the feed water tank 148, is then pressed by a feed water pump 153 through an electromagnetic valve 151b and is jetted into the washing tank 143 through the jetting nozzle 144. The detergent within the detergent tank 149 passes through an electromagnetic valve 151c is pressed by a detergent pump 154 and is then jetted together with the washing water coming from the feed water pump 153 into the washing tank 143 through the jetting nozzle 144. Further, after the washing step ends, the sterilizing liquid within the sterilizing liquid tank 150 is pressed by a sterilizing liquid pump 155 through an electromagnetic valve 151d and is jetted into the washing tank 143 through the jetting nozzle 144.

A heater 156 is provided in the bottom of the above mentioned washing tank 143 so that the washing water and sterilizing liquid accumulated in the washing tank 143 may be heated. Further, the washing water and sterilizing liquid accumulated in the washing tank 143 are led into a three-way switching valve 158 through a drain port 157. This three-way switching valve 158 can be switched to a state that the washing water and sterilizing liquid are drained out of the apparatus by a drain pump 159 and the state that they are circulated by a circulating pump 160.

Also, the same as in the first embodiment, a contact 12 of the read-out circuit 5 reading out the information of the memorizing part 4 within the endoscope 2 is provided within the above mentioned washing tank 143 and is connected to the control part 14 through the read-out circuit 5.

In the washing apparatus of such formation, the washing water, sterilizing liquid and rinsing water are respectively sprayed to make the respective washing, sterilizing and rinsing steps. Further, the respective liquids can be heated by the heater 156. Also, ultraviolet rays can be radiated from the sterilizing lamp 146.

For example, when the sterilizing lamp 146 is lighted at any optional time in the washing sterilizing step, the ultraviolet rays generated by the sterilizing lamp 146 will be radiated onto the endoscope 2 contained in the washing tank 143. Thus, the sterilizing effect by ultraviolet rays is added to the ordinary washing sterilizing effect by the ultraviolet rays from the sterilizing lamp 9 and therefore the sterilizing effect can be elevated without extending the time of the sterilizing step. When the sterilizing lamp 146 is lighted after the washing sterilizing step ends, various germs will be able to be prevented from growing due to water remaining within the washing tank 143.

The same as in the first embodiment, the respective washing and sterilizing steps are made under the conditions adapted to that endoscope on the basis of the proofness data of the endoscope 2.

The warm water and warm sterilizing liquid by heating and the ultraviolet ray radiation by the sterilizing lamp 16 elevate the sterilizing effect but the proofness of the endoscope is a problem. In this embodiment, whether the warm water, warm sterilizing liquid and ultraviolet ray radiation are applicable or not is judged by reading out the information from the memorizing part 4 of the endoscope 2. The data of the patient on whom the endoscope is used are memorized. When the information from this memorizing part 4 is read out, the sterilizing method or the like will be able to be determined in response to the state of the patient on whom the endoscope has been used. Thus, in the washing apparatus of this embodiment, the heating temperature and sterilizing time are properly determined in response to the information from the above mentioned memorizing part 4.

Figure 6:
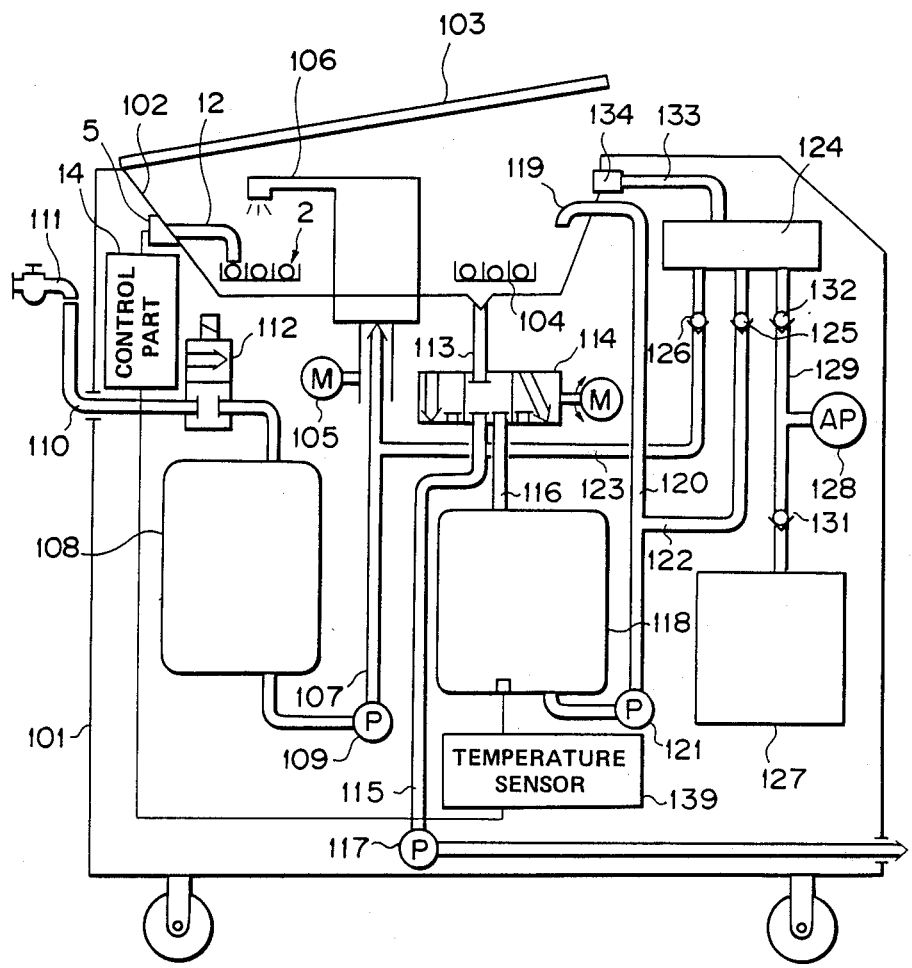
FIG. 6 is an explanatory view showing the formation of a washing apparatus in the fourth embodiment of the present invention.

FIG. 6 shows the fourth embodiment of the present invention.

In FIG. 6, the reference numeral 101 represents a washing apparatus body. A washing tank 102 is formed within this apparatus body 101. The upper opening of this washing tank 102 is closed with a cover 103. A shelf 104 on which the endoscope 2 is to be mounted is set within the washing tank 102. A nozzle 106 rotated and driven by a motor 105 is set substantially in the center of the washing tank 102 and is connected to a water storage tank 108 through a feed water pipe 107. A feed water pump 109 is provided in the course of this feed water pipe 107 so that the water in the water storage tank 108 may be fed to the nozzle 106 by the feed water pump 109. A tap water lead-in pipe 110 is connected to the water storage tank 108 and is to be connected to a tap 111. A switching valve 112 is interposed in the course of the tap water lead-in pipe 110 so that, when a fixed amount of water is accumulated in the water storage tank 108, the introduction of more tap water than the fixed amount will be intercepted.

A drain pipe 113 is connected to the bottom of the above mentioned washing tank 102 and is connected to a waste liquid pipe 115 and return pipe 116 through a three-position switching valve 114. A drain pump 117 is interposed in the course of the waste liquid pipe 115 so that, when the waste liquid pipe 115 is conducted by the above mentioned switching valve 114 while operating this drain pump 117, the liquid within the washing tank 102 will be able to be drained.

A sterilizing liquid tank 118 is connected to the above mentioned return pipe 116. A sterilizing liquid injecting pipe 120 communicating with an injecting nozzle 119 present in the washing tank 102 is connected to the bottom of this sterilizing tank 118. An injecting pump 121 is interposed in the course of this sterilizing liquid injecting pipe 120.

A second sterilizing liquid injecting pipe 122 branching from the sterilizing liquid injecting pipe 120 is provided in the position of the sterilizing liquid injecting pipe 120 positioned on the delivery side more than the injecting pump 121. Further, a second feed water pipe 123 is connected in a position on the delivery side more than the feed water pump 108 in the above mentioned feed water pipe 107. These second sterilizing liquid injecting pipe 122 and second feed water pipe 123 are connected on the delivery sides to a mixing block 124. By the way, check valves 125 and 126 are interposed respectively in the delivery side parts of these second sterilizing liquid injecting pipe 122 and second feed water pipe 123.

Further, a later described ozone generating apparatus 127 and air pump 128 are connected to the mixing block 124 through the same air feeding pipe line 129. The air pump 128 sucks in and presses air within the room and feeds it into the mixing block 124 through the above mentioned air feeding pipe line 129. Two check valves 131 and 132 are interposed in the course of the air feeding pipe line 129 so that no gas may reversely flow to the ozone generating apparatus 127 and air pump 128. For example, a so-called solid high molecular weight electrolyzing method is used for the above mentioned ozone generating apparatus 127. This is a method wherein electrodes are arranged on both sides of a solid high molecular weight electrolyzing membrane (fluorine type cation exchange membrane) and pure water is fed on the anode side. According to this solid high molecular weight electrolyzing method, ozone is generated from pure water by the electrolysis and therefore zone leaner than by the general discharging system is obtained.

On the other hand, a delivery pipe 133 is connected to the above mentioned mixing block 124 and is connected to a tube joint block 134 which is provided on the side surface part of the washing tank 102 and is provided with a plurality of tube joints not illustrated. Washing sterilizing tubes not illustrated are to be removably connected to the respective tube joints. Further, the respective washing and sterilizing tubes are to be connected to the respective channels (such as a sucking channel, air feeding channel and carbon dioxide channel) of the endoscope 2 set in the washing tank 102 to feed washing and sterilizing fluids to them.

Also, the same as in the first embodiment, a contact 12 of the read-out circuit 5 reading out the information of the memorizing part 4 within the endoscope 2 is provided within the above mentioned washing tank 102 and is connected to the control part 14 through the read-out circuit 5.

A temperature sensor 139 sensing the sterilizing liquid temperature is provided in the above mentioned sterilizing liquid tank 118. The detecting output of this temperature sensor 139 is to be input into the above mentioned control part 5.

The operation of the above mentioned washing sterilizing apparatus shall be explained in the following. First of all, the endoscope 2 to be washed and sterilized is set on the shelf 104 of the washing tank 102. The insertable part of the endoscope 2 is wound around the nozzle 106. The washing and sterilizing tubes are connected to the respective channels of the endoscope 2. Thereby, the respective channels are connected to the mixing block 124 through the tube joint block 134.

Now, by opening the switching valve 112, a fixed amount of water accumulated in advance in the water storing tank 108 through the tap water lead-in pipe 110 from the tap 111 is fed to the nozzle 106 through the feed water pipe 107 by the action of the feed water pump 109 and is also fed to the mixing block 124 side. The washing water fed to the nozzle 106 is jetted through the nozzle 106 rotated by the motor 105 to spray and wash all the outer surface of the endoscope 2. The washing water fed to the mixing block 124 side is injected into the respective channels (such as the sucking channel, air feeding channel and carbon dioxide channel) of the endoscope 2 through the tube joint block 134 and washing sterilizing tube from the delivery pipe 133 and is discharged out of the other ends of the openings of the respective channels. Thus, the outside surface of the endoscope 2 and the inside surfaces of the respective channels can be washed. By the way, this washing step is carried out by carrying out in turn the respective steps of pre-washing with the ordinary tap water as it is, real washing by mixing in a detergent and rinsing washing with the tap water as it is.

Also, the washing water drained within the washing tank 102 in these respective washing steps is drained out through the waste liquid pump 117 through the switching valve 114 from the drain pipe 113 in the bottom of the washing tank 102.

After this washing step, the sterilizing step is made. That is to say, the switching valve 114 is switched and the drain pipe 113 in the bottom of the washing tank 102 is intercepted. The operation of the waste liquid pump 117 is stopped. On the other hand, the injection pump 121 is operated to inject the sterilizing liquid into the washing tank 102 through the sterilizing liquid injecting pipe 120 from the sterilizing liquid tank 118. At the same time, the sterilizing liquid is fed also to the mixing block 124 side through the second sterilizing liquid injecting pipe 122. The sterilizing liquid fed to this mixing block 124 side is injected into various channels (such as the sucking channel, air feeding channel and carbon dioxide channel) of the endoscope 2 through the tube joint block 134 and washing sterilizing tube from the delivery pipe 133 to fill the respective channels. The endoscope 2 dipped in the sterilizing liquid within the washing tank 102 is covered on the outer surface with the sterilizing liquid to be sterilized.

Thus, the endoscope 2 is kept for a while in contact on the inside and outside surfaces with the sterilizing liquid to be sterilized.

When this sterilizing treatment ends, the next step of rinsing the sterilizing liquid is made. This rinsing step is the same step of rinsing washing with tap water as it is in the above mentioned washing step. When this rinsing step ends, the next water removing step and drying step are continued.

In the water removing step, the air pump 128 is operated so that room air is sucked and compressed and is fed into various channels (such as the sucking channel, air feeding channel and carbon dioxide channel) of the endoscope 2 set in the washing tank 102 through such gas feeding means as the above mentioned mixing block 124, delivery pipe 133, tube joint block 134. Thus, the rinsing water remaining within various channels (such as the sucking channel, air feeding channel and carbon dioxide channel) is excluded with the fed air pressure. At the same time, the ozone generating apparatus 127 operates to feed the generated ozone to the mixing means consisting of the above mentioned mixing block 124. That is to say, in this step, ozone from the ozone generating apparatus 127 and air from the air pump 128 are fed to the mixing block 124 and are mixed together. This air is sterilized to be nonpoisonous. Further, the water remaining within various channels of the endoscope 2 is removed by the air mixed with this ozone. The air mixed with this ozone is discharged into the washing tank 102 from the ends of the respective channels of the endoscope 2. Thus, as the respective channels of the endoscope 2 are filled with air mixed with ozone, even if germs are present within the channels, they will be able to be sterilized. As the air mixed with ozone is discharged into the washing tank 102 from the end openings of the respective channels to fill the washing tank, the germs remaining in the air can be sterilized.

Further, by continuing this operation for the required time, the drying step drying the interiors of the respective channels of the endoscope 2 can be made.

By the way, even in the above mentioned sterilizing step, if the ozone generating apparatus 127 is operated to feed ozone into the fed sterilizing liquid, ozone will be mixed and dissolved into the sterilizing liquid to be able to give a sterilizing effect by ozone.

The respective washing and sterilizing steps are made under the conditions adapted to the endoscope on the basis of the proofness data of the endoscope 2 read out of the memorizing part 4 and the detected output of the temperature sensor 139.

For example, whether ozone is to be applied or not is determined by the information from the memorizing part 4 of the endoscope 2.

Generally, germs are strong in the proofness against the sterilizing liquid below the optimum growing temperature (below 7° to 10° C.). In this embodiment, as there is no means for heating the sterilizing liquid, the sterilizing liquid temperature may reduce in winter or the like. However, the sterilizing liquid temperature is sensed by the temperature sensor 139 and the sterilizing time is properly extended automatically by the control part 5 in response to the sterilizing liquid temperature.

Figure 7:
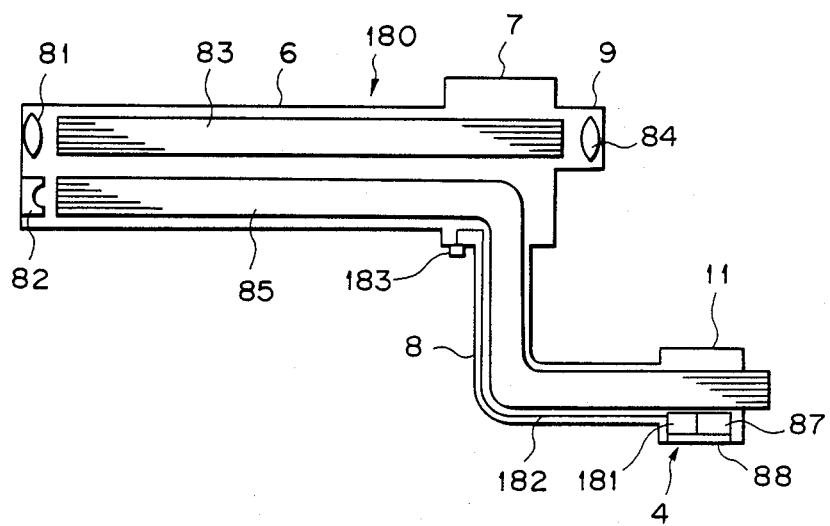
FIG. 7 is an explanatory view showing the formation of an endoscope in the fifth embodiment of the present invention.

FIG. 7 shows the fifth embodiment of the present invention.

In an endoscope 180 in this embodiment, a timer 181 is provided in the memorizing part 4. A resetting switch 183 connected to the above mentioned timer 181 through a signal line 182 to reset the above mentioned timer 181 is provided, for example, in the operating part 7. The elapsed time measured by the above mentioned timer 181 is to be read out together with the proofness data of the endoscope 180 through the contact 88.

The other formations are the same as in the first embodiment.

On the used endoscope, the longer the left time, the more such dirt as a body liquid will solidify to be hard to remove. The longer the time elapses and the nearer to the grown cells, the higher the durability of germs. In this embodiment, the elasped time is measured after the resetting switch 183 is pushed by the timer 181 provided in the memorizing part 4 and is read out of the contact 12. The sterilizing time and washing time can be extended and the sterilizing method can be selected automatically by the control part 14 in response to this elapsed time.

FIGS. 8 to 11 show the sixth embodiment of the present invention.

Figure 8:
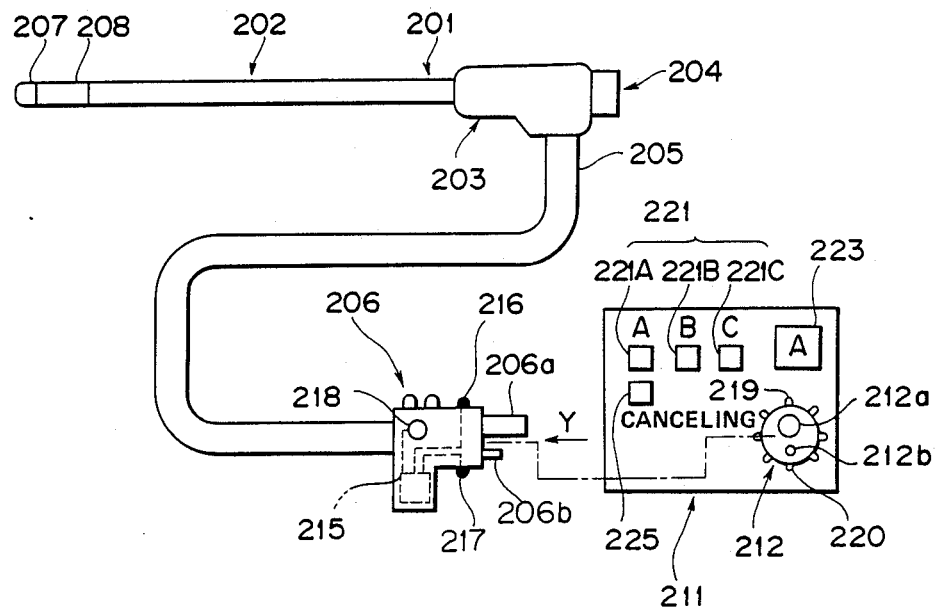
FIGS. 8 to 11 relate to the sixth embodiment of the present invention

As shown in FIG. 8, an endoscope (fiber scope) 201 is provided with an elongate and, for example, flexible insertable part 202 to the rear end of which a thick operating part 203 is connected. The above mentioned insertable part 202 can be inserted through a body cavity from a mouth cavity or the like. An eyepiece part 204 is provided in the rear end part of the above mentioned operating part 203. A flexible universal cord 205 is extended sidewise from the above mentioned operating part 203. A connector 206 is provided at the tip of this universal cord 205. By the way, a rigid tip part 207 and a curvable part 208 adjacent to this tip part 207 and curvable to the rear side are provided in turn on the tip side of the above mentioned insertable part 202. The above mentioned curvable part 208 can be curved vertically and horizontally by rotating a curving operation knob not illustrated provided on the above mentioned operating part 203.

The above mentioned fiber scope 201 is to be connected to a light source apparatus 211 through the above mentioned connector 206. A connector receptacle 212 which can be connected with the connector 206 of the above mentioned fiber scope 201 is provided, for example, on the front surface side of the housing in this light source apparatus 211. By the way, the above mentioned connector 206 is provided with not only an illuminating connector 206a but also an air and water feeding connector 206b. The above mentioned connector receptacle 212 is provided with an illuminating connector receptacle 212a and air and water feeding connector receptacle 212b corresponding to them.

A light source lamp not illustrated is provided within the above mentioned light source apparatus 211. The illuminating light emitted from this light source lamp is to enter the entrance end of a light guide not illustrated inserted through the insertable part 202 of the above mentioned fiber scope 201 and the universal cord 205 through the above mentioned connector receptacle 212 and connector 206. This illuminating light is led to the tip part 207, is emitted from the exit end surface and is radiated onto an object through a light distributing lens not illustrated. An objective lens system not illustrated is fitted within the above mentioned tip part 207. The tip surface of an image guide not illustrated inserted through the above mentioned insertable part 202 is arranged in the image forming position of this objective lens system. The object image by the above mentioned illuminating light is formed on the tip surface of the above mentioned image guide by the above mentioned objective lens system and is led to the above mentioned eyepiece part 204 so as to be able to be observed from this eyepiece part 204.

Figure 9:
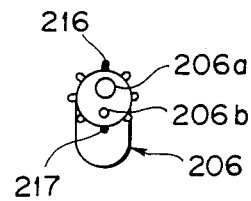
Figure 10:
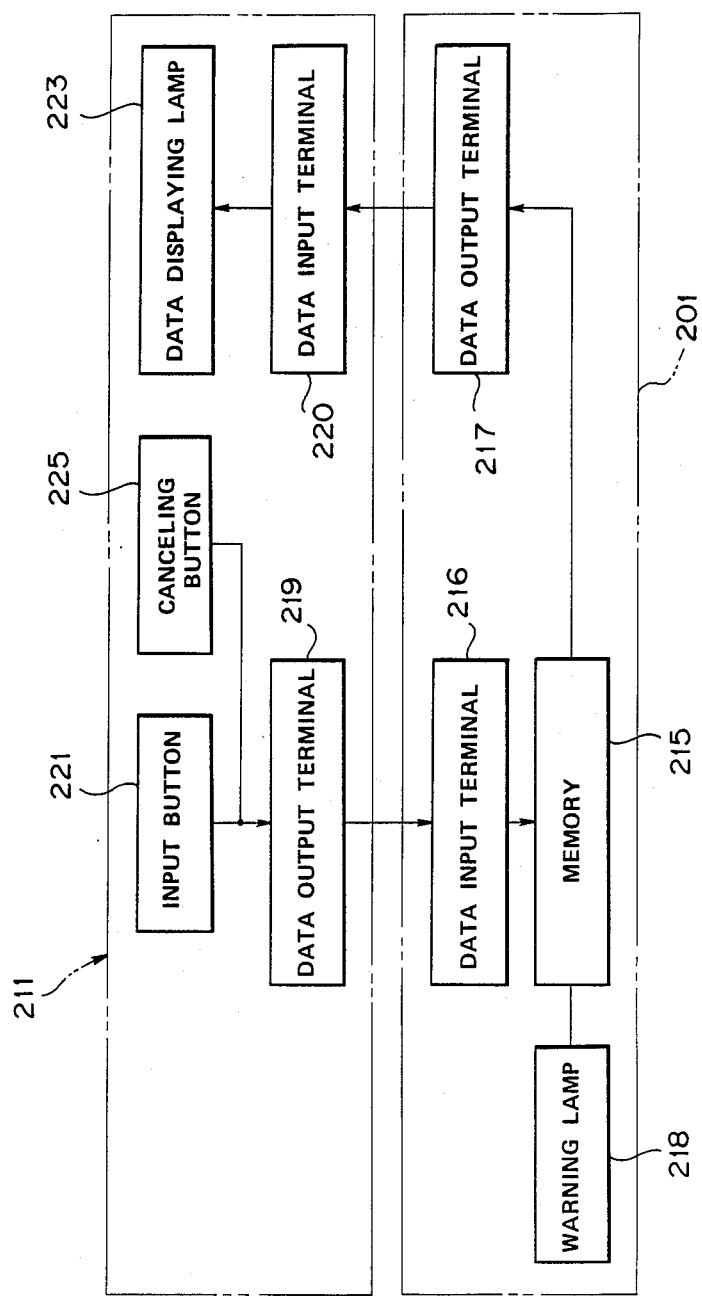

Now, in this embodiment, as shown in FIGS. 8 and 10, a memory 215 memorizing patient data relating to sterilization is contained within the above mentioned connector 106. Also, as shown in FIGS. 8 and 9, a data input terminal 216 for inputting data into the above mentioned memory 215 and a data output terminal 217 for outputting data from the above mentioned memory 215 are provided on the outer periphery on the base side of the illuminating connector 206a and air and water feeding connector 206b of the above mentioned connector 206. A warning lamp 218 is provided on one side of the outer surface of the above mentioned connector 206. As shown in FIG. 10, this warning lamp 218 is connected to the above mentioned memory 215 so as to be lighted, for example, in case patient data relating to sterilization are being memorized in the above mentioned memory 215.

On the other hand, in the above mentioned connector receptacle 212 of the above mentioned light source apparatus 211, in the positions corresponding to the above mentioned data input terminal 216 and data output terminal 217, there are provided a data output terminal 219 and data input terminal 220 to which they are connected. In the above mentioned light source apparatus 211, a plurality of input buttons (switches) 221A, 221B, 221C (which shall be represented by the reference numeral 221 hereinafter) corresponding respectively to the degrees of requiring sterilization or the kinds of sterilization are provided as input means inputting patient data relating to sterilization into the above mentioned memory 215 on the front surface side of the housing. As shown in FIG. 10, these input buttons 221 are connected to the above mentioned data output terminal 219. While the above mentioned fiber scope 201 is connected to the above mentioned light source apparatus 211, when any of the above mentioned input buttons 221 is pushed in response to the disease of the patient using the fiber scope 201, such information relating to the sterilization of the patient as, for example, the degree of requiring sterilization will be input and memorized in the memory 215 provided within the above mentioned connector 206. The above mentioned light source apparatus 211 is provided, for example, on the front surface side of the housing with a data displaying lamp 223 as a displaying means displaying the patient data relating to sterilization memorized in the above mentioned memory 215. As shown in FIG. 10, this displaying lamp 223 is connected to the above mentioned data input terminal 220 so that, when the above mentioned fiber scope 201 is connected to the above mentioned light source apparatus 211, the data memorized in the above mentioned memory 215 will be displayed in this data displaying lamp 223. For example, as shown in FIG. 8, the display by this data displaying lamp 223 will be "A" in case the input button 221A is pushed to input data, will be "B" in case the input button 221B is pushed to input data and will be "C" in case the input button 221C is pushed to input data. A plurality of displaying lamps corresponding to the above mentioned input buttons 221 may be provided so that the lamp corresponding to the input may be lighted. Further, the above mentioned light source apparatus 211 is provided, for example, on the front surface side of the housing with a canceling button 225 for erasing the patient data relating to sterilization memorized in the above mentioned memory 215. As shown in FIG. 10, this canceling button 225 is connected to the above mentioned data output terminal 219. While the above mentioned fiber scope 201 is connected to the above mentioned light source apparatus 211, when the above mentioned canceling button 225 is pushed, the data relating to the sterilization of the patient memorized in the memory 215 provided within the above mentioned connector 206 will be erased.

An example of the operation and action of the endoscope apparatus formed as in the above shall be explained with reference to FIG. 11.

In the case of inspecting the interior of the body cavity of a patient by using the sterilized fiber scope 201, first of all, in the step (abbreviated as S hereinafter) 1, the fiber scope 201 is connected to the light source apparatus 211. Then, in S2, the inspection is made by using the fiber scope 201 and the input button 221 is pushed to input the patient data relating to sterilization. In S3, these patient data are input and memorized in the memory 215 through the data output terminal 219 of the light source apparatus 211 and the data input terminal 216 of the fiber scope 201. When the patient data are memorized in the memory 215, the warning lamp 218 provided in the above mentioned connector 206 will light. When the inspection ends, in S4, the fiber scope 201 is washed and sterilized in response to the patient. After it is washed and sterilized, in S5, the fiber scope 201 is connected to the light source apparatus 11. In S6, the canceling button 225 of the light source apparatus 211 is pushed. Then, in S7, the patient data within the above mentioned memory 215 will be erased and the display of the data displaying lamp 223 of the light source apparatus 211 will be extinguished.

Next, in the case of making an inspection again by using the above mentioned fiber scope 201, in S8, the above mentioned fiber scope 201 is connected to the light source apparatus 11. Then, in S9, whether or not the patient data are memorized in the above mentioned memory 215 is judged and, in case the patient data are not memorized, that is, in case the fiber scope has been sterilized or need not be sterilized, in S10, the patient data will not be displayed in the data displaying lamp 223 of the light source apparatus 211 and, in S17, the inspection is made by using the above mentioned fiber scope 201. Also, together with the inspection, the above mentioned input button 221 is pushed to input the patient data.

On the other hand, in S9, in case the patient data are memorized in the above mentioned memory 215, in S11, the patient data will be displayed in the data displaying lamp 223 of the light source apparatus 211. The warning lamp 218 of the connector 206 will light. there are a case that, after the previous inspection, the washing and sterilization were not made (S4) and a case that the washing and sterilization were made but the patient data of the memory 215 were not erased (S12). In such case, in S13, whether the fiber scope has been washed and sterilized or not is confired and judged by the expert. In case it has not been washed and sterilized, in S14, the fiber scope 201 is washed and sterilized and again confirmed in S12. In case it is confirmed and judged in S13 to have been washed and sterilized, by the judgment of the expert, in S15 the canceling button 225 of the light source apparatus 211 is pushed. Then, in S16, the patient data within the memory 215 will be erased and the display of the data displaying lamp 223 of the light source apparatus will be extinguished. The warning lamp 218 of the connector 206 will go out. In S17, the inspection is made by using the fiber scope 201 and the input button 221 is pushed to input the patient data relating to sterilization.

Thus, in this embodiment, the connector 206 of the fiber scope 201 is provided with the memory 215 memorizing the patient data relating to sterilization so that the patient data may be input by the input button 221 of the light source apparatus and the patient data may be displayed by the data displaying lamp 223. Therefore, before using the fiber scope 201, whether the fiber scope 201 has been used on a patient of a disease likely to be infected, how the fiber scope 201 is to be sterilized or further whether it has been properly sterilized or not can be easily confirmed and the secondary infection can be positively prevented.

Figure 12:
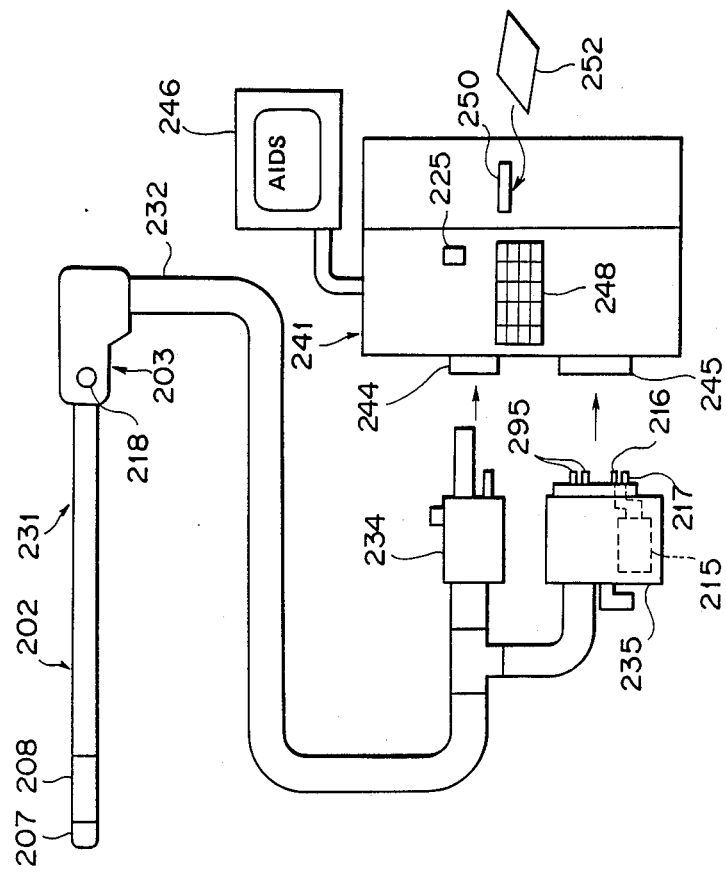
Figure 13:
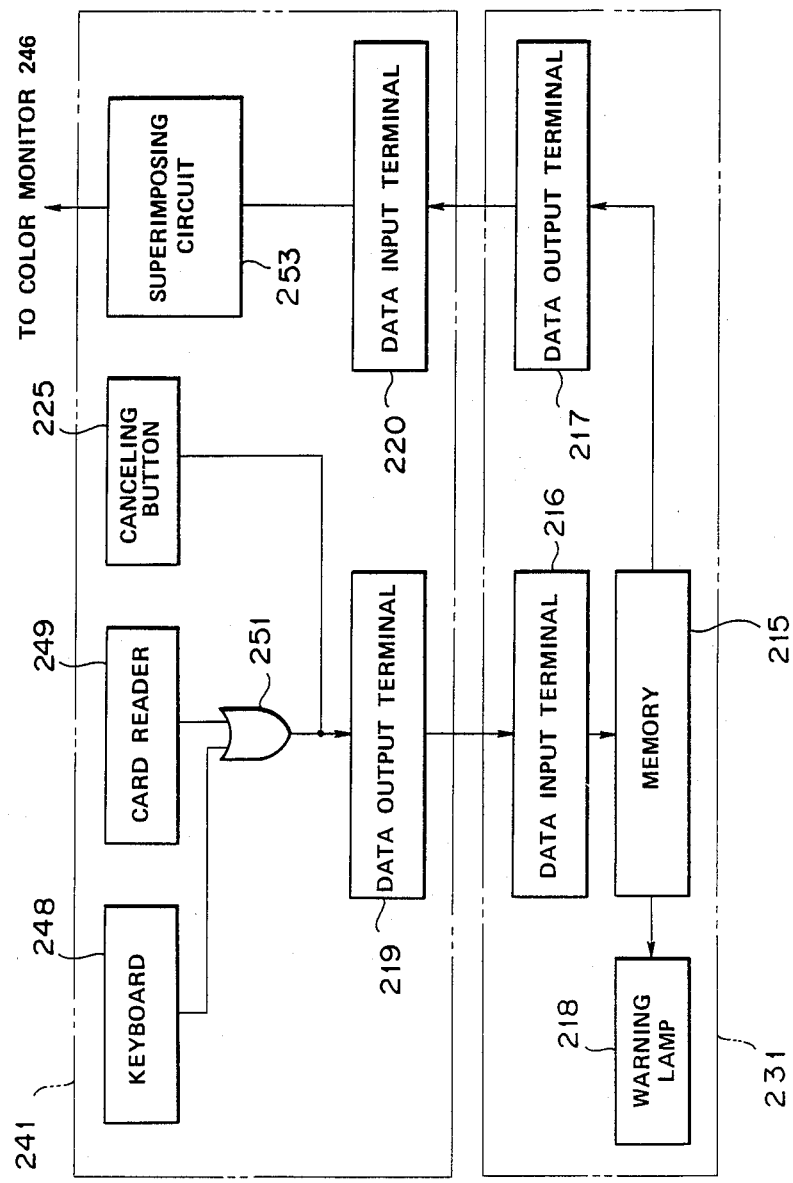

FIGS. 12 to 14 show the seventh embodiment of the present invention.

In this embodiment, an electronic scope is used as an endoscope.

As shown in FIGS. 12 and 14, an electronic scope 231 is provided with a flexible universal cord 232 extended from the operating part. This universal cord 232 is branched on the tip side into two parts. One tip part is provided with an illuminating system connector 234. The other tip part is provided with an electric system connector 235. A light guide 291 inserted through the insertable part 202 and universal cord 232 is connected at the base end to the above mentioned illuminating system connector 234. Within the tip part 207, a solid state imaging device 293 as an imaging means is arranged in the image forming position of an objective lens system 292. This solid state imaging device 293 is connected to terminals 295 provided in the above mentioned electric system connector 235 through signal lines 294 inserted through the insertable part 202 and universal cord 232.

On the other hand, a video processor 241 to which the above mentioned electronic scope 231 is connected is provided with a light source apparatus and signal processing circuit not illustrated and is provided, for example, on the front surface side of the housing with an illuminating system connector receptacle 244 and electric system connector receptacle 245 to which the above mentioned illuminating system connector 234 and electric system connector 235 are to be respectively connected. A color monitor 246 as a displaying means is to be connected to the above mentioned video processor 241. The illuminating light emitted from the light source apparatus within the above mentioned video processor 241 enters the entrance end of the light guide 291 of the electronic scope 231 through the illuminating system connector receptacle 244 and illuminating system connector 234, is led to the tip part 207 by this light guide 291, is emitted from the exit end surface and is radiated onto an object through a light distributing lens 297. The object image by this illuminating light is formed on the above mentioned solid state imaging device 293 by the above mentioned objective lens system 292. This solid state imaging device 293 is driven by the driving signal from a driving circuit not illustrated within the above mentioned video processor 241 connected through the signal lines 294, the read out output signal is input into a video signal processing circuit not illustrated within the above mentioned video processor 241, a video signal is produced by this video signal processing circuit and is input into the above mentioned color monitor 246 and the object image is displayed in this color monitor 246.

By the way, in case a field sequential system is adopted as a color imaging system, the illuminating light will be sequentially switched to such respective color lights as of red, green and blue, the above mentioned solid state imaging device 293 will image objects corresponding to the respective color lights and the respective images corresponding to the respective color lights will be memorized respectively in frame memories, will be simultaneously read out and will be delivered to the color monitor 246. In case a synchronous system is adopted as a color imaging system, a color filter array in which color filters respectively transmitting the respective color lights of red, green and blue are arranged in the form of a mosaic or the like will be provided on the front surface of the solid state imaging device 293.

In this embodiment, as shown in FIGS. 12 and 14, a memory 215 memorizing patient data relating to sterilization is provided within the above mentioned electric system connector 235. This electric system connector 235 is provided with not only terminals 295 for transmitting and receiving signals with the above mentioned solid state imaging device 293 but also a data input terminal 216 for inputting data into the above mentioned memory 215 and a data output terminal 217 for outputting data out of the above mentioned memory 215. Also, in this embodiment, a warning lamp 218 is provided on one side of the outer surface of the operating part 203 of the electronic scope 231 and is connected to the above mentioned memory 215 as shown in FIG. 13 so as to be lighted in case patient data relating to sterilization are being memorized in the above mentioned memory 215.

On the other hand, the electric system connector receptacle 245 of the above mentioned video processor 241 is provided in the positions corresponding to the above mentioned data input terminal 216 and data output terminal 217 with a data output terminal 219 and data input terminal 220 to which they are to be connected. The above mentioned video processor 241 is provided, for example, on the front surface side of the housing with a keyboard 248 as an input means inputting patient data relating to sterilization into the above mentioned memory 215.

The above mentioned video processor 241 is internally fitted with not only the above mentioned keyboard 248 but also a card reader 249 as an input means inputting patient data relating to sterilization into the above mentioned memory 215. An inserting port 50 of the above mentioned card reader 249 is provided, for example, on the front surface side of the housing.

As shown in FIG. 13, the above mentioned keyboard 248 and card reader 249 are connected to the above mentioned data output terminal 219 through an OR gate 251. While the above mentioned electronic scope 231 is connected to the above mentioned video processor 241, when the above mentioned keyboard 248 is operated in response to the disease of the patient on whom the electronic scope 231 is used or when a patient card in which the patient data relating to sterilization are recorded is inserted in the above mentioned card reader, the patient information relating to sterilization will be input and memorized in the memory 215 provided within the above mentioned connector 235.

The same as in the sixth embodiment, the canceling button 225 for erasing the patient data relating to sterilization memorized in the above mentioned memory 215 is provided on the front surface side of the housing and is connected to the above mentioned data output terminal 219 as shown in FIG. 13 so that, while the above mentioned electronic scope 231 is connected to the above mentioned video processor 241, when the above mentioned canceling button 225 is pushed, the patient data relating to sterilization memorized in the memory 215 provided within the above mentioned connector 235 will be erased.

Further, in this embodiment, a superimposing circuit 253 connected to the above mentioned data input end 220 is provided within the above mentioned video processor 241. When the above mentioned electronic scope 231 is connected to the above mentioned video processor 241, the patient data memorized in the above mentioned memory 215 will be input into the above mentioned superimposing circuit 253 so that, by this superimposing circuit 253, the patient data, for example, of the disease name may be superimposed and displayed in the above mentioned color monitor 246 as shown in FIG. 12.

The other formations are the same as in the sixth embodiment.

Figure 11:
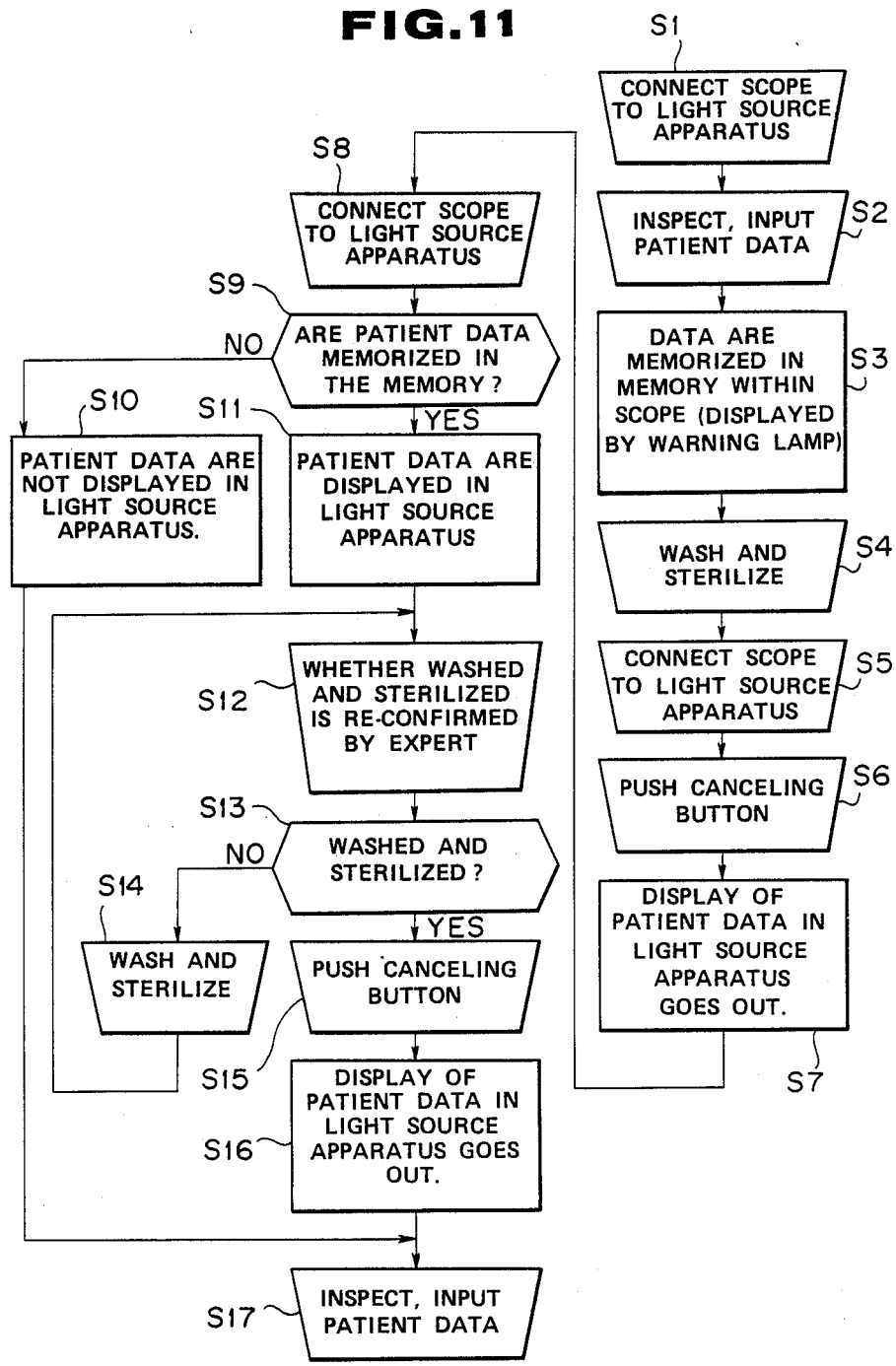

The operation and action of the endoscope apparatus according to this embodiment are substantially the same as in the sixth embodiment shown in FIG. 11. That is to say, in the sixth embodiment, the light source apparatus 211 may be replaced with the video processor 241, the input button 221 may be replaced with the keyboard 248 and card reader 249 and the data displaying lamp 253 may be replaced with the superimposing circuit 253 and color monitor 246.

According to this embodiment, more detailed patient data can be input by the keyboard 248 or card reader 249 and, in case the card reader 249 is used, the data can be automatically input.

FIGS. 15 to 17 show the eighth embodiment of the present invention.

This embodiment is an example of a system combining the endoscope apparatus of the sixth or seventh embodiment with an endoscope washing apparatus.

As shown in FIG. 15, an endoscope washing apparatus 261 is provided with a washing tank 262 which can contain such endoscope as the fiber scope 201 or electronic scope 231, for example, with the insertable part 202 as wound. By the way, an example of the fiber scope 201 is shown in FIG. 15. A scope connector socket 264 which can be connected with the connector 206 of the above mentioned fiber scope 201 or with the electric system connector 235 of the electronicscope 231 is provided on one side of the above mentioned washing tank 262 and is connected with a data reading circuit 265 reading the patient data output form the data output terminal 217 of the scope 201 and a canceling signal output circuit 266 outputting a canceling signal. The patient data read in the above mentioned data reading circuit 265 are input into a discrinating circuit 268 in which the patient data, for example, of the disease name are discriminated. The discriminating output of this discriminating circuit 268 is input into a control circuit 269 so that a proper washing and sterilizing method may be selected by this control circuit 269. In the washing part 270 controlled by the above mentioned control circuit 269, the scope 201 is washed and sterilized according to the method selected by the above mentioned control circuit 269. By the way, the washing and sterilization in the above mentioned washing part 270 are made in the order of a washing step 271, sterilizing step 272, washing step 273 and drying step 274 as shown, for example, in FIG. 16. The above mentioned washing part 270 is connected to the above mentioned canceling signal output circuit 266 so that, when the washing and sterilization end, a signal showing the end of the washing showing the end of the washing and sterilization will be output to the above mentioned canceling signal output circuit 266 from the above mentioned washing part 270 and a canceling signal will be output from this canceling signal output circuit 266.

By the way, in FIG. 16, the reference numeral 281 represents an operating apparatus representing the light source apparatus 211 in the case of using the fiber scope 201 as an endoscope or the video processor 241 in the case of using the electronic scope as an endoscope. In this operating apparatus 281, the input button 221, keyboard 248 and card reader 249 are provided as patient data input means and can be selectively used. The displaying lamp 223 and superimposing circuit 253 are provided as patient data displaying means and can be selectively or both used.

An example of the operation and action of the endscope apparatus formed as in the above shall be explained in the following with reference to FIG. 17.

In the case of inspecting the interior of the body cavity of a patient by using the sterilized fiber scope 201, first of all, in S1, the fiber scope 201 is connected to the operating apparatus 281. Then, in S2, the inspection is made by using the fiber scope 201 and the patient data relating to sterilization are input by such input means as the input button 221, keyboard 248 and card reader 249. In S3, the patient data are input and memorized in the memory 215 through the data output terminal 219 of the operating apparatus 281 and the data input terminal 216 of the fiber scope 201. When the patient data are memorized in the memory 215, the warning lamp 218 provided on the above mentioned connector 206 will light. When the inspection ends, in S21, the fiber scope 201 is fitted to the washing apparatus 261 and the connector 206 of the fiber scope 201 is inserted into the scope connector socket 264 of the washing apparatus 261. Then, in S22, the patient data memorized in the above mentioned memory 215 are read by the data reading circuit 265 through the data output terminal 217 and scope connector socket 264 and are discriminated by the discriminating circuit 268 and further a proper washing and sterilizing method is selected by the control circuit 269. The scope 201 is washed and sterilized according to the method selected by the above mentioned control circuit 269 in the washing part 270 controlled by the above mentioned control circuit 269. When the washing and sterilization in the above mentioned washing part 270 ends, in S23, a signal showing the end of the washing and sterilization will be output to the above mentioned canceling signal output circuit 266 from the above mentioned washing part 270 and a canceling signal will be output from this canceling signal output circuit 266. This canceling signal is input into the above mentioned memory 215 through the above mentioned scope socket 264 and the data input terminal 216 of the fiber scope 201 and, in S24, the patient data within the above mentioned memory 215 are erased.

The operation and action in the case of making the inspection again by using the above mentioned fiber scope 201 are the same as in and after S8 in the sixth embodiment.

By the way, the case of using the fiber scope 201 has been explained in the above. The case of using the electronic scope 231 is also the same.

Thus, according to this embodiment, when such endoscope as the fiber scope 201 provided with the memory 215 is fitted to the washing apparatus 261, the patient data relating to sterilization will be read out of the above mentioned washing apparatus 261, a proper washing and sterilizing method will be automatically selected and the washing and sterilization will be made according to it. After the end of the washing and sterilization, the patient data of the above mentioned memory 215 will be automatically erased.

Therefore, the endoscope can be properly washed and sterilized more positively and simply.

By the way, in the sixth to eighth embodiments, the memory memorizing the patient data relating to sterilization may be provided in the operating part 203 instead of the connector. The means of inputting the patient data into the memory and the means of displaying the patient data memorized in the memory may be provided on the endoscope side, for example, in the operating part 203 instead of the light source apparatus 211 and video processor 241.

As explained above, according to the sixth to eighth embodiments, as the endoscope is provided with a memorizing means which can memorize the patient information relating to sterilization, there are effects that the information of the using patient relating to sterilization can be confirmed and the secondary infection can be prevented.

By the way, the present invention can be applied not only to the case of washing and sterilization with the washing apparatus but also to the case of a sterilizing treatment with a sterilizer.

In this invention, it is apparent that working modes different in a wide range can be formed on the basis of this invention without deviating from the spirit and scope of the invention. This invention is not restricted by its specific working modes except being limited by the appended claims.

What is claimed is:

1. An endoscope, comprising:
   an elongated insertable member having an observing window and illuminating window in a tip portion of said elongated member;
   an observing means for receiving returning light from an object to thereby observe said object, wherein said returning light enters through said observing window;
   an illuminating light output means for emitting an illuminating light from said illuminating window; and
   a memorizing means for memorizing information relating to physical characteristics of said endoscope which are relevant to the washing of said endoscope, including said elongated insertable member, wherein said memorized information is capable of being transferred to a washing apparatus separate from said endoscope.

2. An endoscope according to claim 1, wherein information relating to said washing means relates to at least one condition for washing with water and a condition for washing with washing liquid, sterilizing, rinsing and drying.

3. An endoscope according to claim 1 wherein said memorizing means memorizes proofness information of endoscopes relating to said washing means.

4. An endoscope according to claim 1 wherein said memorizing means memorizes information of using patients relating to washing.

5. An endoscope according to claim 1 wherein said memorizing means has a latch.

6. An endoscope according to claim 1 wherein said memorizing means has a read-only memory (ROM).

7. An endoscope according to claim 1 wherein said memorizing means memorizes encoded information relating to washing.

8. An endoscope according to claim 1 wherein said memorizing means has a time measuring means measuring the elepsed time from a predetermine time.

9. An endoscope according to claim 1 wherein said memorizing means is provided within a connector connectable to a light source apparatus.

10. An endoscope according to claim 1 wherein said observing means has an image forming optical system provided in the tip portion of said insertable member, an eyepiece portion provided on the rear end portion of said insertable member and an image for transmitting optical system transmitting an object image formed by said image forming optical system to said eyepiece portion.

11. An endoscope according to claim 1 wherein said observing means has an image forming optical system provided in the tip part of said insertable part and an imaging means imaging an object image formed by said image forming optical system.

12. An endoscope system, comprising:
   an endoscope having an elongated insertable member having an observing window and illuminating window in a tip portion of said elongated member, an observing means for receiving returning light from an object and for observing said object, said returning light entering through said observing window, an illuminating light output means for emitting an illuminating light from said illuminating window, and a memorizing means for memorizing information relating to washing; and
   an endoscope washing apparatus which is separate from said endoscope having a washing means for washing said endoscope, a read-out means for reading out information memorized in said memorizing means of said endoscope, and a control means for controlling the conditions for washing the endoscope by said washing means resulting from the information read by said read-out means.

13. An endoscope system according to claim 12, wherein said washing means is at least one for washing with water and for washing with liquid, sterilizing, rinsing and drying.

14. An endoscope system according to claim 12 wherein said memorizing means memorizes the proofness information of endoscope.

15. An endoscope system according to claim 12 wherein said memorizing means memorizes the using patient information relating to washing.

16. An endoscope system according to claim 12 wherein said memorizing means has a latch.

17. An endoscope system according to claim 12 wherein said memorizing means has a read-only memory (ROM).

18. An endoscope system according to claim 12 wherein said memorizing means memorizes encoded information relating to washing.

19. An endoscope system according to claim 18 wherein said read-out means has a discriminating means discriminating the code memorized in said memorizing means, a memorizing part in which the information relating to washing corresponding to said code is memorized and a means reading out of said memorizing part the information corresponding to the code discriminated by said discriminating means and transmitting it to said control means.

20. An endoscope system according to claim 12 wherein said memorizing means is provided within a connector connectable to said light source apparatus.

21. An endoscope system according to claim 12 wherein said observing means has an image forming optical system provided in the tip portion of said insertable member, an eyepiece portion provided on the rear end side of said insertable member and an image transmitting optical system for transmitting to said eyepiece portion the object iamge formed by said image forming optical system.

22. An endoscope system according to claim 12 wherein said observing means of said endoscope has an image forming optical system provided in the tip part of said insertable part and an imaging means imaging an object image formed by said image forming optical system.

23. An endoscope system according to claim 12 wherein said washing means has a means radiating ultraviolet rays onto the endoscope.

24. An endoscope system according to claim 12 wherein said washing means has a gas feeding means feeding into the endoscope a gas for dehydrating or drying the endoscope, an ozone generating means and a means mixing ozone generated from said ozone generating means into the gas fed by said gas feeding means.

25. An endoscope system according to claim 12 wherein said control means has a ROM into which a program for washing is written, a RAM in which information relating to washing transmitted from said read-out means is memorized and a CPU controlling said washing means so that, in case said ROM is read out, said RAM is written in and read out and washing is made by the program written in said ROM, the required data may be read out of said RAM and washing adapted to the endoscope may be made.

26. An endoscope system according to claim 12 wherein said washing apparatus has a means erasing the information memorized in said memorizing means further after the washing ends.

* * * * *